United States Patent
Cerullo et al.

(10) Patent No.: US 8,446,580 B2
(45) Date of Patent: May 21, 2013

(54) SYSTEM FOR GENERATING RAMAN VIBRATIONAL ANALYSIS SIGNALS

(75) Inventors: Giulio Nicola Felice Cerullo, Milan (IT); Marco Andrea Arrigo Marangoni, Milan (IT); Fabio Baronio, Flero (IT); Matteo Conforti, Provaglio d'Iseo (IT); Costantino De Angelis, Brescia (IT)

(73) Assignee: Politecnico di Milano, Milan (IT)

( * ) Notice: Subject to any disclaimer, the term of this patent is extended or adjusted under 35 U.S.C. 154(b) by 239 days.

(21) Appl. No.: 13/055,878

(22) PCT Filed: Jul. 29, 2009

(86) PCT No.: PCT/IB2009/006381
§ 371 (c)(1),
(2), (4) Date: Jan. 25, 2011

(87) PCT Pub. No.: WO2010/013118
PCT Pub. Date: Feb. 4, 2010

(65) Prior Publication Data
US 2011/0128538 A1  Jun. 2, 2011

(30) Foreign Application Priority Data
Aug. 1, 2008  (IT) .............................. MI2008A1448

(51) Int. Cl.
*G01J 3/44*  (2006.01)
(52) U.S. Cl.
USPC ........................................................ 356/301

(58) Field of Classification Search
USPC .............................................. 356/301, 72–73
See application file for complete search history.

(56) References Cited

U.S. PATENT DOCUMENTS

| | | | | |
|---|---|---|---|---|
| 6,516,127 | B1 * | 2/2003 | Fluck et al. | 385/132 |
| 6,934,020 | B2 * | 8/2005 | Shimada | 356/301 |
| 2008/0037599 | A1 * | 2/2008 | Ma et al. | 372/21 |

OTHER PUBLICATIONS

Akimov et al., "Photonic-Crystal Fiber Sources for Nonliner Spectroscopy," Vibrational Spectroscopy, vol. 42, No. 1, pp. 33-40, 2006.
Ganikhanov et al., "Broadly Tunable Dual-Wavelength Light Source for Coherent Anti-strokes Raman Scattering Microscopy," Optics Letters, vol. 31, No. 9, pp. 1292-1294, May 2006.
Imeshev et al., "Generation of Dual-Wavelength Pulses by Frequency Doubling with Quasi-Phase-Matching Gratings," Optics Letters, vol. 26, No. 5, pp. 268-270, Mar. 2001.

(Continued)

*Primary Examiner* — Tarifur Chowdhury
*Assistant Examiner* — Abdullahi Nur
(74) *Attorney, Agent, or Firm* — King & Spalding

(57) ABSTRACT

A system for generating signals for Raman vibrational analysis, particularly for a CARS microscope or spectroscope of an external specimen, the system including a laser source capable of emitting at least one fundamental optical pulse in a first band of fundamental frequencies including at least one first and one second fundamental frequencies; a second-harmonic generating system including at least one nonlinear optical crystal for converting the at least one fundamental optical pulse into a first and a second-harmonic optical pulse; and a Raman vibrational analysis apparatus capable of receiving the first and second second-harmonic pulses and direct them toward the specimen.

14 Claims, 5 Drawing Sheets

OTHER PUBLICATIONS

Marangoni et al., "Tunable Narrow-Bandwidth Picosecond Pulses by Spectral Compression of Femtosecond Pulses in Second-order Non-linear Crystals," 2008 Conference on Quantum Electronics and Laser Science Conference on Lasers and Electro-Optics, CLEO/QELS, 2008.

Marangoni et al., "Synthesis of Picosecond Pulses by Spectral Compression and Shaping of Femtoscecond Pulses in Engineered Quadratic Nonlinear Media," Optics Letters, vol. 34, No. 3, pp. 241-243, Feb. 2009.

Porter et al., "Coherent Anti-Strokes Rama Scattering Microscopy with Spectrally Tailored Ultrafast Pulses," Review of Scientific Instruments, vol. 76, No. 4, pp. 43108-1-43108-5, Mar. 2005.

Zhao et al., "Tunable Dual-Signal PPLN Optical Parametric Generator by Using an Acousto-Optic Beam Splitter," Journal of Optics, vol. 9, No. 3, pp. 235-238, Mar. 2007.

* cited by examiner

SYSTEM FOR GENERATING RAMAN VIBRATIONAL ANALYSIS SIGNALS

FIELD OF THE INVENTION

The present invention relates to a nonlinear vibrational spectroscopy and microscopy apparatus. In particular, the present invention concerns a highly frequency-tunable and sensitive coherent anti-Stokes Raman scattering microscopy and spectroscopy apparatus.

BACKGROUND ART

Molecular vibrations have oscillation periods that reflect the molecular structure, and may hence be used for detection and unique identification of molecules. Particularly, vibrational spectroscopy allows unique identification of molecules having high environmental and biological impact, and may therefore find application in microscopy without fluorescent markers and to environmental and biomedical diagnostics.

Among the various vibrational spectroscopy techniques, Coherent Anti-Stoke Raman Scattering (CARS) is a powerful technique for acquiring chemically selective images of biological and chemical specimens. CARS is based on the Raman effect and uses two laser beams, a pump beam at a center frequency $\omega_p$ and a Stokes beam at a center frequency $\omega_s$. The optical process is a nonlinear third-order process: a pump photon and a Stokes photon interact with a specimen and excite the vibrational level at frequency $\Omega_{vib}=(\omega_p-\omega_s)$. A third photon, at frequency $\omega_p$, also coming from the pump beam, interacts with the excited vibrational level and stimulates the emission of a coherent photon at anti-Stokes frequency $\omega_{as}=(2\omega_p-\omega_s)$. As a result, when $\Omega_{vib}$ is resonantly tuned with a given vibrational mode associated with a molecule, a CARS signal of anti-Stokes frequency $\omega_{as}$ is obtained, which may be utilized for high-sensitivity detection of molecules characterized by the vibrational frequency $\Omega_{vib}$. The CARS technique may be used in both microscopy and spectroscopy, to obtain images of in vitro and in vivo cell structures, in sensor technology or for detection of molecules having a high environmental impact.

In spite of its high potential, the CARS technique still suffers from certain implementation difficulties. Since CARS is a nonlinear third-order process, high peak powers, which can be obtained with short light pulses, are necessary to obtain significant efficiencies. On the other hand, there exists a lower limit for pulse duration: since Raman transitions have typical line widths of the order of a few cm$^{-1}$, pump and Stokes pulses of narrow bandwidth are necessary, which correspond to minimal durations of a few picoseconds for efficiently exciting the system and allowing discrimination of close vibrational frequencies. Practical applications of the CARS technique generally require two or more synchronized laser sources emitting picosecond pulses, with a frequency difference tunable in a broad range. E. O. Potma and Sunney Xie in "*CARS Microscopy for Biology and Medicine*", published in Optics & Photonics News, November 2004, pages 40-45, gives a brief overview of the evolution of certain CARS schemes.

The paper "*High-sensitivity coherent anti-Stokes Raman scattering microscopy with two tightly synchronized picosecond lasers*" by E. O. Potma et al., published in Optics Letters, vol. 27, No. 13 (2002), pages 1168-1170, describes a CARS scheme that uses two picosecond Ti:sapphire lasers synchronized via a phase-locked-loop. The CARS image is formed by a sample scan realized by piezo transducers.

In "*An Epi-Detected Coherent Anti-Stokes Raman Scattering (E-CARS) Microscope with High Spectral Resolution and High Sensitivity*" by Ji-Xin Cheng et al., published in The Journal of Chemical Chemistry B, vol. 105, No. 7 (2001), pages 1277-1280, CARS detection is carried out using two picosecond Ti:sapphire laser sources synchronized via a "lock-to-clock" system.

Patent application US 2008/0037595 discloses a system for generating an electromagnetic pump field at a first frequency and a Stokes field at a second frequency for a CARS system. The system includes an optical parametric oscillator based on a periodically poled nonlinear crystal which is synchronously pumped by the second harmonic output of a picosecond laser to obtain a pulsed signal at a signal frequency (providing the pump field) and a pulsed signal at an idler frequency (providing the Stokes field). A tuning system adjusts the temperature of the nonlinear crystal to change the difference between the signal frequency and the idler frequency.

Some authors have suggested the use of a single ultra-short (femtosecond) pulse for the whole CARS process. The paper "*Single-pulse coherently controlled nonlinear Raman spectroscopy and microscopy*", by N. Dudovich et al., published in Letters to Nature, vol. 418 (2002), pages 512-514, discloses an experimental CARS spectroscopy system consisting in a mode-locked Ti-sapphire laser, which emits 20 fs pulses at 80 MHz, a programmable pulse shaper (an electronically controllable spatial light modulator) and a photodetector. Spectral data is obtained by shaping the excitation pulse to resolve the weak resonant signal from the strong nonresonant noise.

A CARS system that uses a single fs source associated with a pulse shaper is also disclosed in WO 2004/068126.

Periodically poled crystals (pp) are frequently used as nonlinear optical materials and are typically more efficient in second harmonic (SH) generation, than crystals of the same material with no periodic structure.

The spectral and temporal properties of a femtosecond pulse may be significantly changed by quadratic interactions under large group velocity mismatch (GVM). The paper "*Narrow-bandwidth picosecond pulses by spectral compression of femtosecond pulses in a second-order non linear crystal*" by M. Marangoni et al., published in Optics Express, vol. 15, No. 14 (2007), pages 8884-8891, describes a technique for spectral compression of broadband femtosecond pulses based on the nonlinear optical second harmonic (SH) generation process under large GVM between interacting pulses. A high GVM implies a very narrow bandwidth in which the phase matching condition is fulfilled, and therefore a narrow bandwidth generation of picosecond SH pulses. This technique provides a "spectral compression" that can use a broadband fundamental frequency (FF) pulse to generate narrowband SH pulse with high spectral tunability. SH conversion is obtained using a pp stoichiometric lithium tantalate crystal (pp-SLT). Wavelength tuning is obtained by changing the phase-marching condition in the crystal and changing the pump wavelength.

"*Designer femtosecond pulse shaping using grating-engineered quasi-phase-matching in lithium niobate*" di Kornaszewski et al., published in Optics Letters, vol. 33, No. 4 (2008), pages 378-380, describes the use of an aperiodically poled lithium niobate crystal for generation of femtosecond pulses with fully engineered intensity and phase profiles using second harmonic generation by an erbium-doped optical fiber laser.

SUMMARY OF THE INVENTION

Inventors have observed that the use of two sources to generate a pump signal and a Stokes signal requires a synchronization device, such as a phase-locked loop or a lock-to-clock, which adds complexity and bulk to the measuring apparatus and increases manufacturing costs.

Inventors have also remarked that a CARS apparatus that uses a parametric oscillator for pump and Stokes signal generation requires optical synchronization between the oscillator cavity and the laser source cavity, and therefore a control electronics to hold the locked position. The presence of two synchronized cavities increases the complexity and costs of this CARS apparatus. Furthermore, this system does not allow to synthesize a third pulse at the anti-Stokes frequency.

Inventors have realized that the use of a source that emits femtosecond pulses provides a relatively broad frequency (or wavelength) band, containing a range of vibrational energies, e.g. from 100 to 1500 $cm^{-1}$, associated with the "signature" of a variety of chemical species.

Inventors have conceived a system for generating signals for Raman vibrational analysis which comprises a second-harmonic (SH) generating system that includes at least one nonlinear optical crystal, the SH generating system being capable of converting a fundamental optical pulse, within a frequency band comprising at least two optical fundamental frequencies, into at least two optical pulses at two different higher-order, preferably second-order, harmonics of the respective fundamental frequencies. The first and second pulses at the first and second higher-order harmonic frequency may be used as pump and Stokes frequencies to be introduced in a CARS microscope or spectroscope, and may be more generally used in Raman spectroscopy-based vibrational analysis. Advantageously, in the system for generating signals for vibrational analysis in accordance to the present invention, the two pulses at pump and Stokes frequencies respectively are synchronized or quasi-synchronized with each other (i.e. they temporally overlap), because they are generated from a common fundamental pulse and frequency-converted by the SH generating system. Advantageously, the two SH pulses are synthesized from the same laser pulse and are hence phase-coherent with each other. Particularly, if the fundamental pulse for Raman excitation is a pulse centered around the fundamental frequency (FF), $\omega_f$, with a bandwidth from $\omega_f-\Delta\omega$ to $\omega_f+\Delta\omega$, it is possible to synthesize, by means of the SH generating process, two narrow-band pulses at pump ($\omega_p$) and Stokes ($\omega_s$) frequencies, with $\omega_p$ and $\omega_s$ being from $2\omega_f-2\Delta\omega$ to $2\omega_f+2\Delta\omega$. For example, if the spectral width of the fundamental pulse is 1500 $cm^{-1}$ (i.e., $2\Delta\omega=1500$ $cm^{-1}$), $\omega_p$ and $\omega_s$ may have a wavelength difference of up to 3000 $cm^{-1}$. Therefore, the use of the SH generating system allows generation of CARS signals for detection of a wide range of molecules and materials.

Preferably, the spectral width of the fundamental pulse (i.e. the pulse bandwidth) falls is of from 100 to 1500 $cm^{-1}$. Preferably, the spectral width of SH pulses is of from 1 to 20 $cm^{-1}$. In some preferred embodiments, the fundamental pulse has a relatively broad bandwidth and the SH generating system converts the fundamental pulse into at least two SH pulses having a significantly narrower band, i.e. narrower by a factor of at least ten, preferably by a factor of from about ten to one hundred, with respect to the bandwidth of the fundamental pulse.

Preferably, the laser source is adapted to emit a femtosecond pulse beam (also known as pulse train), e.g. from 10 to 100 fs. Preferably, the pulses generated by the SH generating system are of the picoseconds order, e.g. 1-10 ps.

The SH generating system comprises at least one nonlinear optical crystal apt to convert a pulse within a frequency band comprising at least two fundamental frequencies into two pulses, each at a second harmonic frequency of the respective fundamental frequency in the crystal.

According to a preferred embodiment, the SH generating system comprises a pair of nonlinear optical crystals, each crystal of the pair being apt to convert a fundamental frequency pulse into a second-harmonic frequency pulse having twice the frequency of the respective fundamental frequencies. Preferably, each of the nonlinear crystals comprise a periodically poled nonlinear crystal, with periodic reversal of the sign of nonlinear optical susceptibility in the direction of propagation of the fundamental beam.

According to a further embodiment, the SH generating system comprises a nonlinear optical crystal apt to convert a pulse comprising two fundamental frequencies into two second-harmonic pulses, each at twice the frequency of the respective fundamental frequency. Preferably, said crystal comprises an aperiodically poled nonlinear crystal, with aperiodic reversal of the sign of nonlinear optical susceptibility in the direction of propagation of the fundamental beam.

Inventors have found that the fact that the two pump and Stokes beams, which are generated by at least one nonlinear optical crystal with fundamental pulses impinging thereon, are synchronous and phase-coherent can be advantageously used to generate a local oscillator in a heterodyne CARS spectroscopy/microscopy detection scheme resulting in a significantly amplified CARS signal.

In one embodiment, the system for generating optical signals for Raman vibrational analysis comprises a laser source and a SH generating system that includes first, second and third nonlinear optical crystals, each of the crystals being apt to receive first, second and third fundamental pulse beams, respectively, comprising respective first, second and third fundamental frequencies. The first crystal is apt to generate a first SH pulse beam at a first SH frequency of the first fundamental frequency, the second crystal is apt to generate a second SH pulse beam at a second SH frequency of the second fundamental frequency, and the third crystal is apt to generate a third SH pulse at a third SH frequency of the third fundamental frequency, wherein said third SH frequency is the anti-Stokes frequency with respect to the first and second SH frequencies. The crystals are preferably periodically poled crystals with periodic reversal of the sign of nonlinear optical susceptibility in the directions of propagation of the fundamental beam. Preferably, the first, second and third fundamental pulse beams derive from the same fundamental beam generated by a laser source, i.e. the laser source is apt to generate an optical pulse beam in a frequency band comprising the three fundamental frequencies. Alternatively, the laser source is apt to generate two optical fundamental pulse beams having two distinct frequency bands.

According to a further embodiment, the SH generating system comprises two nonlinear optical crystals, i.e. a first crystal apt to receive a first fundamental pulse beam within at least one band of frequencies comprising two fundamental frequencies and a second crystal apt to receive a second pulse beam within a band of frequencies comprising a third fundamental frequency, wherein the first crystal is preferably an aperiodically poled crystal, with aperiodic reversal of the sign of optical susceptibility along the direction of propagation of the fundamental beam and is apt to generate a SH pulse beam at a first and a second SH frequency of the first and second fundamental frequencies respectively, wherein the second crystal, preferably a periodically poled crystal, is apt to generate a SH pulse beam at a third SH frequency of the third fundamental frequency, and wherein said third SH frequency is the anti-Stokes frequency with respect to the first and second SH frequencies.

The first and second fundamental pulse beams may be derived from the same beam generated by a laser source, or be two fundamental beams, preferably generated by the same laser source with distinct frequency bands, a first band comprising the first and second fundamental frequencies and a second band comprising the third fundamental frequency.

BRIEF DESCRIPTION OF THE FIGURES

Further characteristics and advantages of the invention will be apparent from the following detailed description, which is made with reference to non-limiting embodiments thereof, and to the accompanying figures, in which.

DETAILED DESCRIPTION OF PREFERRED EMBODIMENTS

Figure 1:
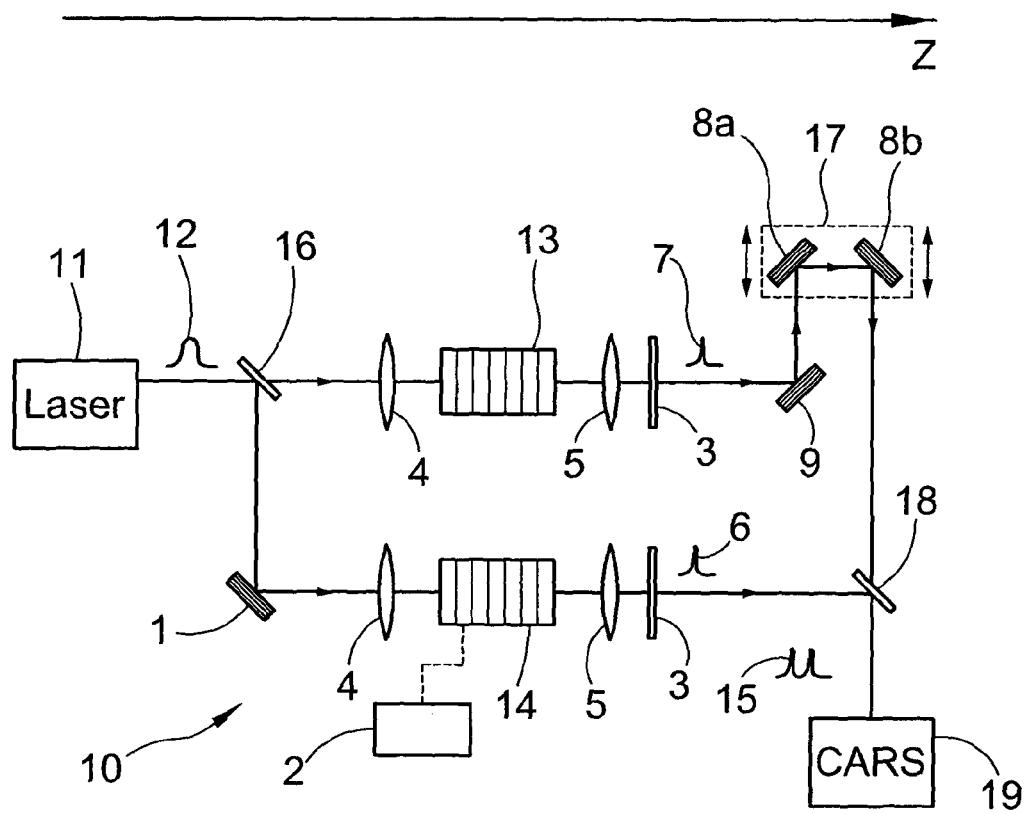
FIG. 1 is a diagrammatic view of a system for generating pulses for CARS according to an embodiment of the present invention.

FIG. 1 is a diagrammatic view of a system 10 for generating pulses for CARS vibrational spectroscopy/microscopy according to an embodiment of the present invention. A laser source 11 is apt to generate pulses 12 within a band of fundamental frequencies, and of duration of femtosecond (fs) order. Preferably, the laser source is apt to generate pulses of from 5 fs to 100 fs, preferably of from 10 fs to 50 fs. For example, the laser source is a Ti:sapphire laser oscillator capable of emitting pulses with a FWHM of 20 fs at 100 MHz, centered at a wavelength of 800 nm. The incoming beam is split by an optical power divider device 16, such as a 50/50 beam splitter, which splits the power of beam 12 to form two pulse beams, a first beam incident upon a first nonlinear crystal 13 and a second beam incident upon a second nonlinear crystal 14, optionally after being deflected by a mirror 1. According to the present embodiment, the first and second nonlinear crystals form a second-harmonic (SH) generating system.

The crystals 13 and 14 are disposed longitudinally with respect to the incident beams so that the beam passes through each crystal along its length and emerges from an end face opposite to the beam entry end face. The direction of incidence and propagation of laser beams in crystals is indicated by the Z axis and is the same for both crystals in the illustrated example, i.e. the two crystals are disposed substantially parallel to each other. However, it should be noted that it is not necessary that the two fundamental beams propagate in parallel directions.

Preferably, the first and second nonlinear crystals 13, 14 are ferroelectric crystals, which have a structure with periodic space-modulation of the sign of nonlinear optical susceptibility in the direction of incidence of the interacting laser beam (i.e. they are periodically poled, or pp). Periodic susceptibility modulation periodically changes the sign of nonlinear optical coupling coefficient in the direction of incidence of the optical beam. As a result, the polarization response of the crystal is periodically phase-matched with the incoming pulses. This provides a positive net flow of energy between the incoming beam and the one that comes out of the crystal and the intensity of the generated wave quadratically increases with the distance covered by the incident beam in the nonlinear crystal. The phase-matching or quasi-phase-matching condition, which efficiently generates the outgoing beam, depends on the poling period, i.e. the period of inversion of the nonlinear optical susceptibility. Without wishing to be bound by any theory, sum frequency generating processes are produced in the crystal, which convert frequency pairs within the broad band of the fundamental incident field into a single higher-harmonic frequency.

Preferably, the crystals have a second-order nonlinearity with space-modulation of the second-order susceptibility tensor, $\chi^{(2)}$. Periodic space-modulation of the material polarization may be obtained by known methods, e.g. by periodically changing the orientation of the optical axis of the crystal through the application of alternate strong electric fields (generally of the order of kV/mm). The periodic $\chi^{(2)}$ variation structure is often designated as a periodic grating structure with a poling period corresponding to the sum of the length of two opposite and adjacent domains.

The femtosecond pulses 12 impinge upon each crystal 13 and 14 with a band of fundamental frequencies, for example in a range of frequencies from about 700 nm to 900 nm, comprising at least one first and one second fundamental frequencies, $\omega_{f1}$ e $\omega_{f2}$. The first crystal 13 exhibits a periodic susceptibility reversal characterized by a first period, $A_1$, and is apt to convert the pulses at the first fundamental frequency, con, into pulses centered at the second-harmonic frequency, i.e. $\omega_1 = 2\omega_{f1}$. The second crystal 14 exhibits a periodic susceptibility reversal characterized by a second period, $V_2$, and is apt to convert the pulses at the second fundamental frequency, $\omega_{f2}$, into pulses centered at the second-harmonic frequency, i.e. $\omega_2 = 2\omega_{f2}$.

Optionally, two focusing or recollimating lenses 4 and 5 are placed along the optical path of the incident beam upstream and downstream from each of the nonlinear crystals 13 and 14 respectively. Preferably, at the exit of each crystal and downstream from the focusing lenses 5, the SH beam passes through an optical short-wave pass (SWP) filter 3 which is apt to cut off the fundamental frequencies and transmit the second-harmonic frequency.

The pulses generated by the two crystals are, or anyway may be, easily synchronized because they come from one incident beam and may be used as pump and Stokes fields. Furthermore, the pulses generated by the two crystals are phase-coherent, still owing to their common origin from the same incident laser beam. In the example of FIG. 1, the crystal 13 generates the pump field of frequency $\omega_1 = \omega_p$ (pulse 7) and the crystal 14 generates the Stokes field (pulse 6) of frequency $\omega_2 = \omega_s$. However, this is not a limiting example, and the CARS signal generating system might also use the first crystal 13 for generating Stokes pulses and the second crystal 14 for generating pump pulses.

Pump and Stokes pulses are recombined by an optical recombination device 18, such as a beam splitter or a dichroic mirror, to form two spatially and temporally overlapping pulse trains 15 at frequencies $\omega_p$ e $\omega_s$, and they form a pulse beam for Raman vibrational analysis to be supplied to a per-se known CARS microscope or spectroscope 19. A specimen to be analyzed (not shown), containing a molecule with Raman-active vibrational energy, is placed in the CARS apparatus 19. The vibrational analysis pulse beam 15 is directed to the specimen in a known manner. The two pulse trains, preferably having a ps-order duration, may be thus used for detecting and identifying chemical/biological species at a frequency $\Omega_{vib}= (\omega_p-\omega_s)$.

Although the pump and Stokes pulses are obtained from a single fundamental beam, an optical path difference between the incident beams, e.g. caused by a different distance from the exit of each crystal and the dichroic mirror 18 or between the beam splitter 16 and the entry of the crystals 13 and 14 respectively, may cause a little optical path difference between the beams 6 and 7 at the point in which they are to be combined (e.g. in the device 18) to form the optical beam for Raman vibrational analysis 15. For this purpose, the system 10 optionally comprises an optical delay device 17, such as a free-space optical delay device with an optical path length adjustable by two mirrors 8a and 8b placed at a distance adjustable for example by means of mechanical translation systems. In the implementation of FIG. 1, the pump beam 7 impinges upon a mirror 9 that deflects it towards the optical delay device 17.

It shall be noted that optical path length adjustment, if required, is typically of the mm order, as simple experimental arrangements may lead to the design of "quasi" equal optical paths for the two beams (with tolerances of a few mm). Adjustments of this order typically require the use of technologically simple devices, such as an optical delay line, that may be simply implemented in the system. Conversely, the synchronization of two beams emitted from two fs laser sources (e.g. emitting pulses with a duration of a few tens of fs) require an fs-order synchronization corresponding to a control of the laser cavity length of the order of the wavelength, which is obtainable with complex devices such as active feedback loop devices including piezoelectric transducers.

For the frequencies $\omega_p$ and $\omega_s$ to be different, the nonlinear crystals may be formed with the same material, but with different reversal periods $\nabla_1$ e $\nabla_2$. Alternatively, the crystals may be formed with two different materials and be characterized by different periods.

Preferably, the crystals 13 and 14 have a plurality of ferroelectric domains, with poling occurring across the whole length passed through by the incident laser beams. Spatial modulation periods are preferably of from 3 to 35 µm.

Advantageously, the physical characteristics of the nonlinear crystal (e.g. its length in the direction of propagation of the beam, i.e. the Z axis) are selected for a significant group velocity difference to exist between the fundamental pulses for SH generation and the SH pulses. Advantageously, conversion efficiency, which is defined as the ratio of the power of the fundamental beam to the power of the beam that comes out of the crystal is at least 10%, preferably at least 20%. Examples of periodically poled (pp) ferroelectric crystals with relatively high GVM values are the pp lithium niobate (pp-LN), the pp stoichiometric lithium tantalate (pp-SLT) or the pp potassium titanyl phosphate (pp-KTP), optionally doped with MgO or ZnO to increase crystal resistance to any photorefractive damage caused by beam incidence.

Table 1 gives, by way of example, a few numerical values for the frequencies of the input pump and Stokes pulses, which are suitable to probe a pair of typical vibrational frequencies, $\Omega_{vib}$, i.e., C—H (single bond) and C=C (double bond) stretching vibrations, in the case of a system as shown in FIG. 1, comprising two pp-LN at room temperature.

The values of Table 1 are:

$\lambda_{fs}^P$: first fundamental wavelength belonging to the spectrum of the femtosecond pulse from which the second-harmonic is generated by synthesis in the first crystal, i.e. the "pump" crystal (e.g. the crystal 13 of FIG. 1);

$\lambda_{ps}^P$: first wavelength of the picosecond pulses generated by the first crystal, $\lambda_{ps}^P=\frac{1}{2}\lambda_{fs}^P$;

$\lambda_{fs}^S$: second fundamental wavelength belonging to the spectrum of the femtosecond pulse from which the second-harmonic is generated by synthesis in the second crystal, i.e. the "Stokes" crystal (e.g. the crystal 14 of FIG. 1);

$\lambda_{ps}^S$: second wavelength of the picosecond pulses generated by the second crystal, $\lambda_{ps}^S=\frac{1}{2}\lambda_{fs}^S$;

$\nabla^P$ and $\nabla^S$ grating periods of the first and second crystals respectively, required for the synthesis of $\lambda_{ps}^P$ e $\lambda_{ps}^S$ respectively.

TABLE 1

| | | Pump | | | Stokes | | |
|---|---|---|---|---|---|---|---|
| Vibration type | $\Omega_{vib}$ (cm$^{-1}$) | $\lambda_{fs}^P$ [nm] | $\lambda_{ps}^P$ [nm] | $\Lambda^P$ [µm] | $\lambda_{fs}^S$ [nm] | $\lambda_{ps}^S$ [nm] | $\Lambda^S$ [µm] |
| C—H stretching | 2800 | 1550 | 775 | 18.99 | 1980 | 990 | 29.32 |
| C=C stretching | 1500 | 1550 | 775 | 18.99 | 1754 | 877 | 24.33 |
| Fingerprint region | 300 | 1514 | 757 | 18.00 | 1586 | 793 | 19.97 |

Preferably, the CARS signal generating system 10 is frequency-tunable, i.e. the pump or Stokes frequencies may be varied to obtain a tunable probe frequency $\Omega_{vib}=(\omega_p-\omega_s)$.

Figure 4:
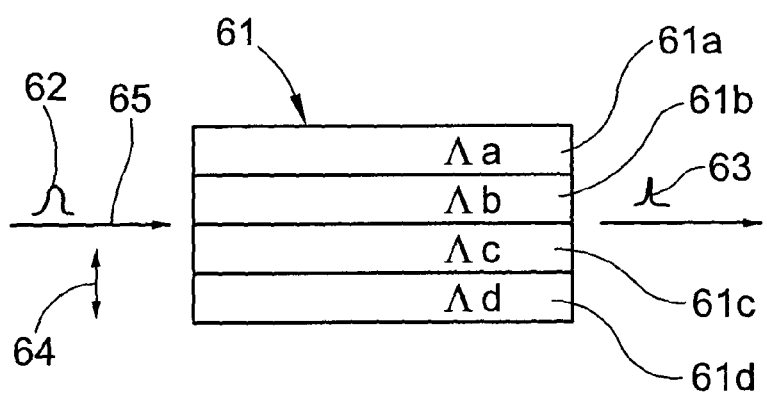
FIG. 4 schematically illustrates a nonlinear crystal with multiple periodicity and its interaction with the incident beam.

Frequency tuning may be obtained using a SH generating system comprising at least one nonlinear optical crystal, particularly of ferroelectric type, whose structure comprises a plurality of longitudinal sections arranged along the direction of propagation of the fundamental beam, each section being characterized by a nonlinear optical susceptibility reversal period. FIG. 4 schematically shows a nonlinear crystal 61 with multiple periodicity, which comprises a plurality of longitudinal sections (four sections 61a-61d are shown by way of example) arranged in the direction of the incident beam 65, each of the sections having a periodic grating with period $\nabla_a, \ldots \nabla_d$, respectively. By changing the point of incidence of the pulse beam 62 in a direction 64 transverse (and preferably orthogonal) to the direction of incidence 65 and to the orientation of the sections, e.g. using an appropriate, possibly motor-driven, mechanical translating system, the period of the crystal through which the incident beam 62 passes changes, and then the SH frequency generated by the beam 63 that comes out of the crystal changes.

Figure 5:
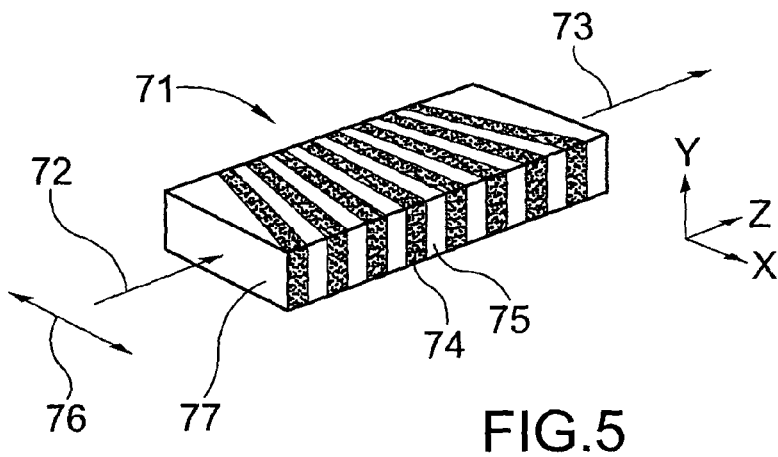
FIG. 5 schematically illustrates a nonlinear crystal with continuous periodicity variation (of the "fan-out" type) and its interaction with the incident beam.

Referring to FIG. 5, alternatively, frequency tuning may be obtained by means of a nonlinear optical crystal, particularly of ferroelectric type, 71, with "fan-out" grating, whose period changes in the lateral direction in the crystal, i.e. in a direction transverse to the direction of propagation of the incident beam. The fan-out grating of FIG. 5 comprises a sequence of ferroelectric domains 74 and 75 with nonlinear optical susceptibilities of opposite signs disposed in a direction orthogonal (designated by Y in the figure) to the direction of incidence 72 (along the Z axis). The regions 74 and 75 have a fan arrangement with respect to the direction of incidence 72. The SH frequency may be tuned by changing the point of incidence at the entry face of the crystal 77 in the direction 76, transverse and preferably orthogonal to the direction of propagation of the beam and parallel to the entry face 77 of the crystal, until the desired phase-matching condition is achieved for a given nonlinear optical interaction that corresponds to a certain SH frequency.

A crystal with a plurality of sections having different periods or a crystal with a fan-out grating arrangement may be used in the SH generating conversion system of the CARS signal generation system of FIG. 1. In accordance with one embodiment, the crystal 14 (13) is a crystal as described with reference to FIG. 4 or 5, in other words a crystal apt to generate a Stokes (pump) frequency tunable within a given frequency range. As an example, the crystal 14 (13) is a pp-LN with a variable grating period of from 18 to 30 nm in a direction orthogonal to the direction of propagation.

According to a preferred embodiment, at least one of the two crystals is in thermal contact with a heating element (not shown), which may be temperature-controlled or be introduced into a temperature-adjustable oven (not shown). In FIG. 1, the crystal 14 is electrically connected to a control unit 2 in turn connected to a heating element (not shown) or to an oven (not shown) to control the crystal temperature. A temperature variation leads to a change in the phase-matching condition and in the wavelength of the second-harmonic generated by the crystal having a grating structure with period $\nabla$. In ferroelectric crystals, it is advantageous to use temperature variation for fine tuning of the SH wavelength (e.g. within about 10 nm). For instance, by increasing the temperature of a pp-SLT crystal from 20° C. to 200° C. with $\Lambda=16.4$ µm, the SH wavelength may be changed from 690 nm to 704 nm. A greater SH wavelength change (e.g. exceeding 30-50 nm) generally requires a greater temperature change, which may be undesired in certain applications.

However, certain embodiments of the present invention include the use of wavelength-tunable SH generation systems, in which tuning is only obtained by a temperature variation of at least one nonlinear crystal.

Figure 2:
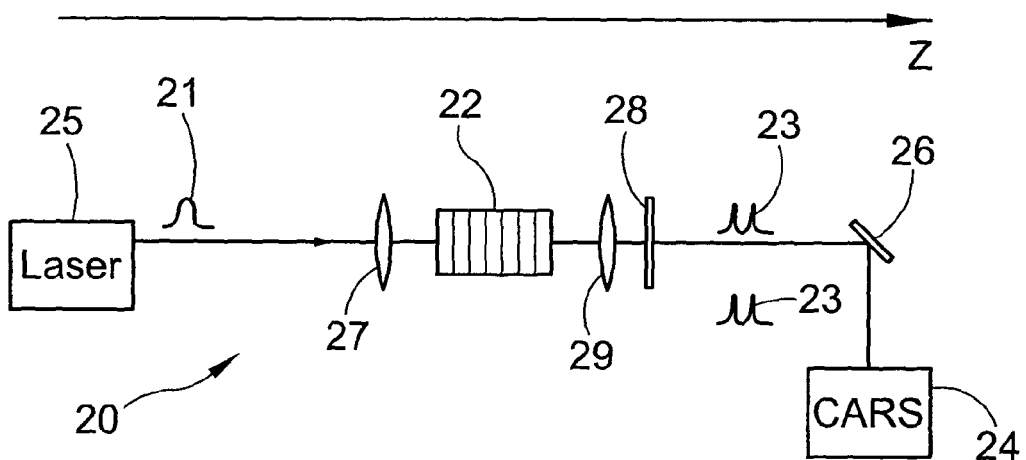
FIG. 2 is a diagrammatic view of a system for generating pulses for CARS according to a further embodiment of the present invention.

FIG. 2 is a diagrammatic view of a system for generating pulses for CARS according to a further embodiment of the present invention. The system 20 comprises a SH generating system, realized with a single nonlinear optical system 22 which is apt to generate, from an incident pulse 21 that covers a band of fundamental frequencies comprising first and second fundamental frequencies, a SH pulse 23 whose spectrum is composed of two peaks at two (different) SH frequencies, $\omega_1$ and $\omega_2$. The incident pulse 21 is emitted from a laser source 25 and is preferably of the fs order. In this SH generation scheme, a single nonlinear crystal simultaneously generates both the pump and the Stokes pulses. The nonlinear crystal 22 provides aperiodic reversal of the sign of nonlinear optical susceptibility in the direction of propagation of the beam (which is designated in the figure by the Z axis); preferably, it is an aperiodically poled or chirped periodically poled ferroelectric crystal. The aperiodically poled crystal may have a grating arrangement, whose period varies, in the direction of propagation of the optical beam, in a linear or exponential manner or according to a predetermined function. For example, the aperiodically poled crystal may have a grating resulting from the overlap of at least two regular (i.e. constant-period) gratings having different periods.

An example of aperiodically poled ferroelectric crystal is an aperiodically poled lithium niobate crystal with a "quasi-phase-matched" grating, in which the period varies linearly from an initial value at the entry of the crystal to a final value at the exit of the crystal in the direction of propagation.

The crystal 22 is disposed longitudinally with respect to the incoming beam 21, i.e. along the axis Z, so that the beam passes along its length and emerges from an end face of the crystal opposite to the beam entry end face.

The pulse trains 23 at pump and Stokes frequencies are optionally backscattered by a mirror 26 which deflects them towards a CARS microscope or spectroscope 24, known per se, in which the specimen to be analyzed is placed.

Optionally, two focusing or recollimating lenses 27 and 29 are placed along the optical path of the beam upstream and downstream from the nonlinear crystal 22 respectively. Preferably, at the exit of the crystal 22 and downstream from the focusing lens 29, the SH beam passes through an optical Short-Wave Pass (SWP) filter 28 which is apt to cut off the fundamental frequencies and transmit the SH frequencies.

The frequency conversion system as shown in FIG. 2 allows generation of two optical SH pulse beams of different colors, having a relatively narrow bandwidth (by doubling the frequency of two portions of the—relatively broad bandwidth—spectrum portions centered at two different input fundamental frequencies) and overlapping in both time and space. The output pulses are synchronized because they are generated by the same fundamental frequency pulse, and being frequency-converted by the same crystal, cover the same optical path along the crystal. The two SH pulses are also phase-coherent because they are generated from the same laser beam.

Figure 7:
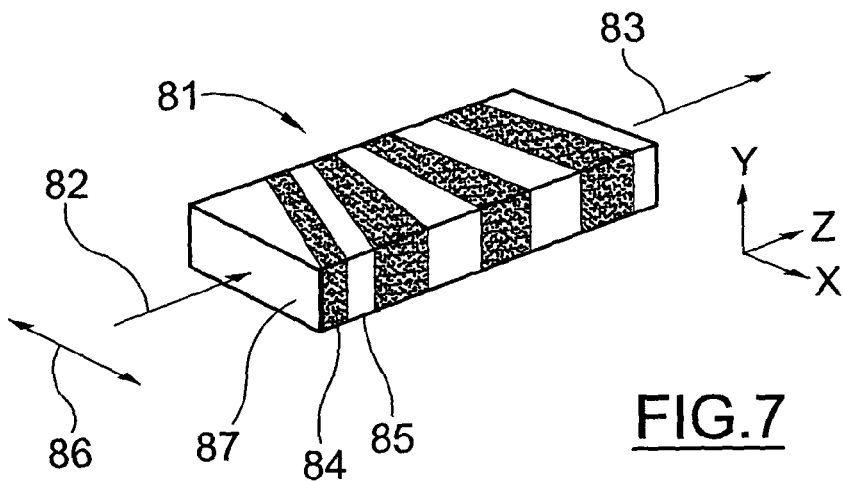
FIG. 7 schematically illustrates an aperiodic nonlinear crystal of the "fan-out" type.

The frequency conversion system is preferably tunable, i.e. the pump and/or Stokes frequencies generated by the interaction of the incident beam with the aperiodically poled crystal can be tuned within a range of frequencies, e.g. from 100 to 1500 $cm^{-1}$. The system can be tuned, for instance, using a fan-out aperiodically poled crystal, as shown in FIG. 7. The fan-out grating comprises a sequence of parallel domains 84 and 85 arranged in a direction orthogonal (designated by Y in the figure) to the direction of incidence 82, along the Z axis, and having an opposite sign of nonlinear optical susceptibility. The regions 85 have a fan arrangement with respect to the direction of incidence 82. The regions 85 and 84 have a continuous variation of poling period in a direction orthogonal to the direction of propagation of the incident beam. The second-harmonic pump or Stokes frequency can be tuned by changing the point of incidence at the entry face of the crystal 87 in the direction 86 substantially parallel to the entry face and transverse (preferably orthogonal) to the direction of incidence, until the desired phase-matching condition is achieved for a suitable difference between the frequencies of the two peaks of the SH pulse. More generally, tuning may be obtained by changing the period of the sign of nonlinear susceptibility in a direction transverse to the direction of the fundamental beam.

Inventors have observed that certain commercially available fs pulse generating laser sources have a spectral bandwidth that is not broad enough to allow pump and Stokes generation by SH generation processes with a relatively large difference $(\omega_p-\omega_s)$, e.g. higher than 400-500 cm$^{-1}$, and thus the analysis of a certain class of molecules of possible interest (such as hydrocarbons or macro-proteins) may be not possible. The inventors have understood that pulses having more distant colors can be synthesized using a laser source that is apt to simultaneously generate two synchronous and phase-coherent pulses with two different fundamental frequency bandwidths, wherein the first of said fundamental pulses passes through a SH generating system apt to generate two pump pulses and a first Stokes pulse $\omega_p$ e $\omega_{s1}$, and the second of said fundamental pulses passes through a different nonlinear crystal apt to generate a second-harmonic signal at a Stokes frequency $\omega_{s2}$, other than the Stokes frequency $\omega_{s1}$. In such a system, appropriate selection of the nonlinear crystals allows generation of a possibly tunable CARS signal, that may be selected between two different vibrational frequency ranges.

Figure 3:
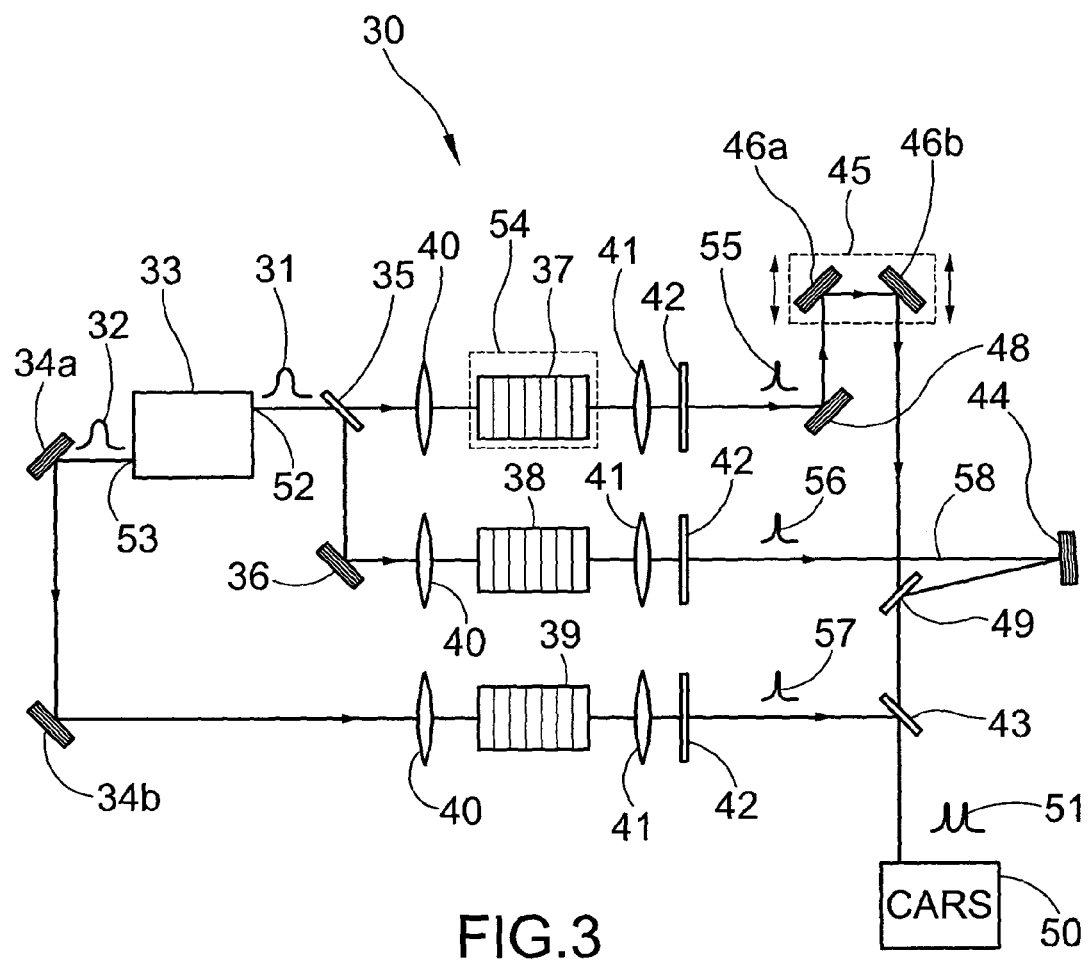
FIG. 3 is a diagrammatic view of a system for generating pulses for CARS according to a further embodiment of the present invention.

FIG. 3 schematically illustrates a system 30 for generating CARS signals according to an embodiment of the present invention. A laser source 33 is apt to generate a first pulse train 31 within a fs time range, and a second pulse train 32 within a fs time range, wherein the second pulse train 32 has a fundamental frequency band different from the frequency band of the first pulse train 31. The first fundamental pulse signal 31 is within a frequency band that includes at least two fundamental optical frequencies and the second fundamental pulse signal 32 is within a frequency band that includes at least one third fundamental optical frequency, other than the first two fundamental optical frequencies. For example, the generation of two different frequency bands may be obtained by supercontinuum generation in a nonlinear optical fiber.

In an embodiment, the laser source 33 is a commercial erbium-doped fiber oscillator with two amplified outputs 52 and 53. For example, the pulse train 31 has a duration of 65 fs, a repetition rate of 100 MHz, an energy of 2.5 nJ (corresponding to an average power of 250 mW) and a carrier wavelength of 1550 nm. The second pulse train 32 is generated as a pulse train identical to the first pulse train and is then coupled into a highly nonlinear optical fiber which is apt to generate (through effects such as supercontinuum generation and/or soliton-self-frequency-shift) tunable pulses of from 1100 to 2000 nm, with durations of about 35 fs and energies of ~200 pJ (about 20 mW average power).

The first fs pulse train 31 forms the incoming beam for the SH generating system comprising a pair of periodically poled ferroelectric crystals 37 and 38 with periods $\nabla_1$ e $\nabla_2$, respectively, in the direction of propagation of the beam. In particular, the pulse train 31 is power-split by a power splitter 35 into two pulse beams, wherein the first beam is directed to crystal 38 and the second beam is directed to crystal 37, after being deflected by a mirror 36. Preferably, the first and second fundamental beams pass through a focusing lens 40 before entering each of the two crystals. An optical signal of ps frequency $\omega_p$ is emitted at the output of the crystal 37 to form the pump signal 55, while an optical signal 56 of ps frequency $\omega_{s1}$ is emitted at the output of the crystal 38 to form the (first) Stokes signal. Preferably, a focusing lens 41 and an optical SWP (Short-Wave-Pass) filter 42 located downstream therefrom, apt to cut off the fundamental frequencies and transmit the SH frequency, are placed in the optical path of each of the pump and Stokes beams.

Optionally, the crystal 37 apt to generate the pump pulse 55 is placed in a temperature-adjustable oven 54 for fine frequency tuning (by changing the phase-matching condition of the crystal).

The second pulse train 32 generated by the laser source 33 at the exit 53 passes through an assembly of mirrors 34a and 34b which deflect the signal and direct it toward a third nonlinear optical crystal 39, which is apt to generate a pulse 57 at a second harmonic frequency of the third fundamental frequency. Preferably, the crystal 39 is a periodically poled ferroelectric crystal with a period $\nabla_3$, other than $\nabla_1$ and $\nabla_2$, in the direction of propagation of the incoming signal, i.e. the optical path. Preferably, two focusing lenses 40 and 41 are placed along the optical path of the incident beam upstream and downstream from the crystal 39 respectively. Preferably, at the exit of the crystal and downstream from the focusing filter, the beam passes through an optical SWP filter 42 which is apt to cut off fundamental frequencies and transmit the SH frequency.

For example, the optical beams 31 and 32 are emitted with a spot size of about 1 mm and pass through the focusing lenses 40 with a focal length from 50 to 150 mm so as to produce an optical beam in which the beams in the focal plane have spot sizes of the order of 25-75 μm.

For example, the crystals 37, 38 and 39 may be selected from the group pp-LN, pp-LT (lithium tantalate) and pp-KTP, with or without the addition of oxides (such as MgO) to increase optical damage resistance.

The nonlinear crystals 37, 38 and 39 are arranged longitudinally with respect to the incident beams so that the beam passes through each crystal along its length and emerges from an end face opposite to the beam entry end face.

In the CARS signal generating system of FIG. 3, the SH generating system is apt to generate first Stokes pulses whose frequency differs from the pump pulses by a value $\Omega_{vib1}=(\omega_p-\omega_{s1})$ and second Stokes pulses whose frequency differs from the pump pulses by a value $\Omega_{vib2}=(\omega_p-\omega_{s2})$. Preferably, $\Omega_{vib1}<\Omega_{vib2}$, for example $\Omega_{vib1}\leqq 450$ cm$^{-1}$ and $\Omega_{vib2}>450$ cm$^{-1}$. For example, if the laser source is an erbium-doped fiber oscillator, the second pulse train 32 is tunable in the wavelength region from 1550 to 2000 nm, and therefore it is possible to synthesize picosecond Stokes pulses having frequencies lower than pump frequencies by more than 3000 cm$^{-1}$.

It will be appreciated that the two pulse trains impinging upon the SH generating system formed by three nonlinear crystals 37, 38 and 39, are phase-coherent, because they come from the same laser source. The vibrational frequencies $\Omega_{vib1}$ and/or $\Omega_{vib2}$ may be tuned within a frequency range, by selecting nonlinear crystals 38 (37) and/or 39 with variable periods, for example having the configurations described with reference to FIG. 4 or 5.

By referring back to FIG. 3, the mirror 26 is optionally of "flip" type, i.e. it allows to enable or disable the optical path of the second fundamental beam 32, depending on the vibrational frequency to be analyzed.

According to a preferred embodiment, the pump signal 55 generated by the crystal 37 is deflected by a mirror 48 located downstream from the optical SWP filter 42, and directed into an optical delay device 45 with the purpose of adjusting the optical path to cause it to be equal to the length of the optical path of the Stokes signal 56 at frequency $\omega_{s1}$ (or alternatively with the Stokes signal 57 at frequency $\omega_{s2}$) and thus to allow the two pulse trains to overlap in time. In the embodiment shown in the figure, the optical delay device 45 is formed by a pair of orthogonal mirrors 46a and 46b, that are mounted on a manually or electronically controlled mechanical translating system. Dichroic flip mirrors 43 and 49 may be selectively added or removed to and from the optical beam path, for allowing the switch among the signals 56 and 57 at Stokes frequencies $\omega_{s1}$ and $\omega_{s2}$, so as to form a pump and Stokes pulse train 51 that can detect "low" and "high" frequency vibrational modes, respectively. Optionally, as a further means for adjusting the optical path length of the pump and Stokes beams, the signal 56 covers an additional variable-length optical path before being deflected by a movable mirror 44. The pulse train 51 is supplied to a CARS microscope or spectroscope 50.

In the embodiment of FIG. 3, the first, second and third nonlinear crystals 37, 38 and 39 form a SH generating system.

Figure 6:
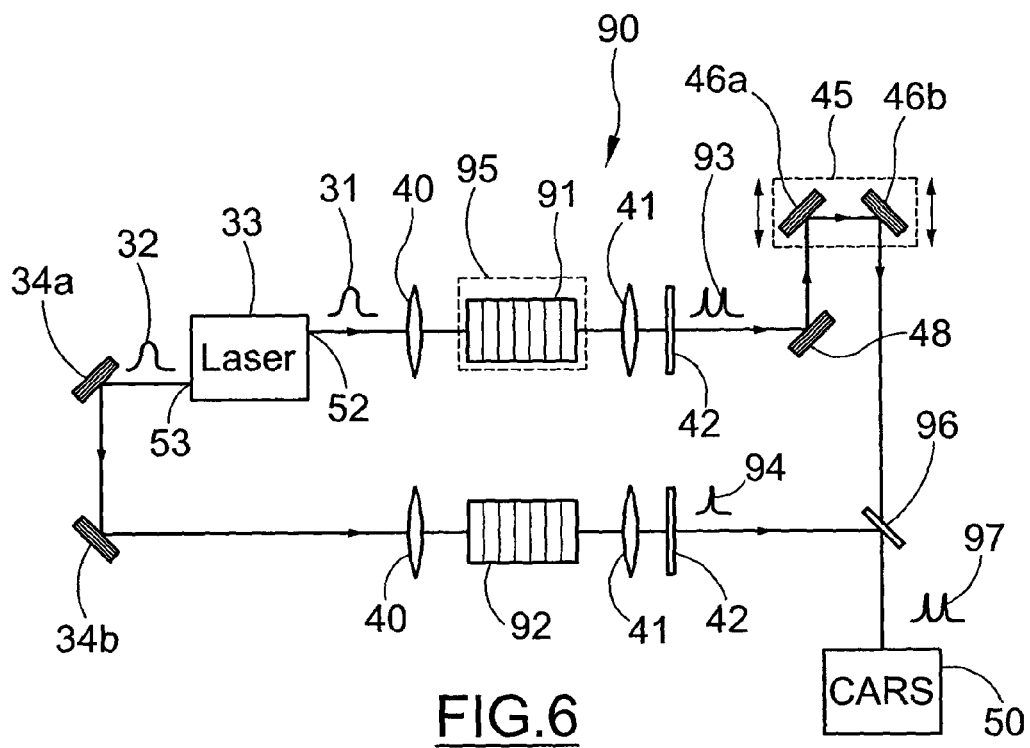
FIG. 6 is a diagrammatic view of a system for generating pulses for CARS according to a further embodiment of the present invention.

FIG. 6 schematically illustrates a further embodiment of the present invention. Like reference numerals will be used to designate system components that are common with those of the system described with reference to FIG. 3 or have equivalent functions, detailed description thereof being omitted hereinafter. The main difference from the embodiment of FIG. 3 is that, in the SH generating system that generates the pump signal and the first Stokes signal at frequency $\omega_{s1}$, a single aperiodic non linear crystal 91, as described with reference to FIG. 2, is used. The second pulse train 32 generated by the laser source 33 passes through a second nonlinear optical crystal 92 apt to generate a pulse at a second harmonic frequency of the third fundamental frequency of the second fundamental signal 32. Preferably, the crystal 92 is a periodically poled ferroelectric crystal, with poling in the direction of propagation of the incoming fundamental optical beam. The pulse beam 93 generated by the aperiodic crystal 91 comprises two overlapping pulse trains at frequencies $\omega_p$ e $\omega_{s1}$, whereas the pulse beam 94 generated by the crystal 92 is centered at a Stokes frequency, $\omega_{s2}$, different from $\omega_{s1}$. A dichroic filter 96, e.g. of SWP type, may be selectively added or removed to or from the optical beam path, allowing the signal 94 to be blocked or transmitted. In the operating position in which the signal 94 is transmitted, the dichroic filter 96 cuts off the pulse at frequency $\omega_{s1}$ so as to form a CARS signal 97 at pump frequency $\omega_p$ and Stokes frequency $\omega_{s2}$. The signal 97 comprising two pulse trains at $\omega_p$ and $\omega_{s1}$ or $\omega_p$ and $\omega_{s2}$, is supplied to a CARS microscope or spectroscope 50.

According to a preferred embodiment, the CARS signal at the probe frequency $\Omega_{vib1,2}=(\omega_p-\omega_{s1,2})$ is tunable. Frequency tuning may be obtained, for instance, using at least one non-linear optical crystal (91 and/or 92) having multiple-sections periodic grating or a fan-out arrangement. Alternatively or in addition, as shown in FIG. 6, at least one crystal of the SH generating system (e.g. 91) is thermally controlled by a temperature-controlled oven 95 so that a temperature variation corresponds to a change in the poling period.

Inventors have understood that the fact that the two pump and Stokes beams generated by at least one nonlinear crystal with fs pulses impinging thereon are phase coherent can be advantageously employed to generate a local oscillator in a heterodyne CARS spectroscopy/microscopy detection scheme resulting in a significantly amplified CARS signal.

Figure 8:
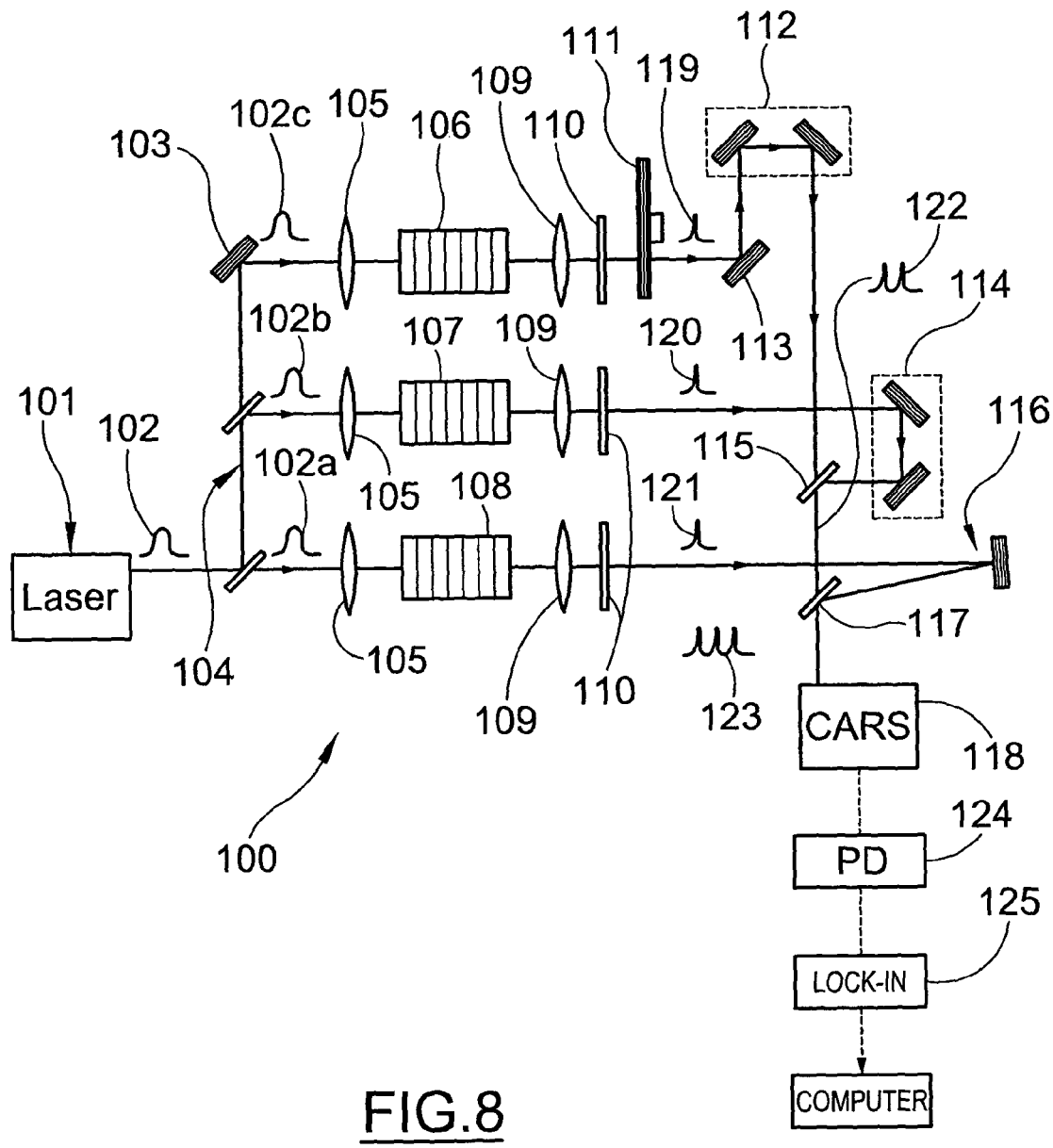
FIG. 8 is a diagrammatic view of a system for generating pulses for CARS that uses an optical heterodyne according to an embodiment of the present invention.

FIG. 8 schematically shows a system for generating pulses for CARS 100 that uses an optical heterodyne according to an embodiment of the present invention. A laser source 101 generates a fundamental pulse beam 102 within a frequency band comprising at least three fundamental optical frequencies ($\omega_{f1}$, $\omega_{f2}$ and $\omega_{f3}$). For example, the laser source is a Ti:sapphire source emitting a pulse signal within a frequency band of from 700 to 900 nm. Alternatively, the laser source is a source as described with reference to FIGS. 3 and 6, which is apt to emit two pulse signals at two different frequency bandwidths, the first comprising at least two fundamental optical frequency and the second comprising at least one third fundamental optical frequency, different from the first two fundamental optical frequencies.

Preferably, the pulses of the fundamental beam 102 have a femtosecond duration.

The fundamental pulse signal 102 passes through an optical power divider device (e.g. a beam splitter) 104 which splits the power of the beam 102 into beams 102a and 102b and deflects a portion of the beam 102b to a mirror 103 which in turn deflects it towards a first nonlinear crystal 106. The fundamental beams 102a and 102b impinge upon second and third nonlinear crystals 107 and 108 respectively. Optionally, before entering the nonlinear crystals, the fundamental beams 102a-102c pass through a collimating/focusing lens 105. Lenses 109 and SWP filters 110 are also optionally arranged at the exit of the crystals, along respective optical paths.

Each of the nonlinear crystals 106, 107 and 108 is apt to generate a pulse at a SH frequency of a fundamental frequency of the incident fundamental beam. Preferably, the crystals 106, 107 and 108 are periodically poled ferroelectric crystals, characterized by three different poling periods. Preferably, the SH pulses generated by the SH generating system are of the ps order.

The first crystal 106 generates a SH pulse at pump frequency $\omega_p$, whereas the second crystal 107 generates a SH pulse at Stokes frequency, $\omega_{s1}$.

The structural characteristics (e.g. grating period) of the third nonlinear crystal 108 are selected in view of generating SH pulses at anti-Stokes frequency, $\omega_{as}=(2\omega_p-\omega_{s1})$. Anti-Stokes pulses are used as a local oscillator in a heterodyne detection scheme. In this scheme, the optical CARS signal formed by the two pump and Stokes signals, which are generated by the first two crystals, interferes with the optical signal of the local oscillator provided by the anti-Stokes signal generated by the third crystal 108 in a detector. In the detected signal, the electric field of the CARS signal, $E_{CARS}$, interferes with the field of the electric signal of the local oscillator, $E_{OL}$. Since the electric field $E_{OL}$ is generally much stronger than the electric field $E_{CARS}$ the component $E_{OL}^2$ shall be conveniently eliminated to increase the resolution of the CARS signal. The continuous component $E_{OL}^2$ can be eliminated from the detected signal by introducing a modulation in the optical signal generated by the SH generating system. In the embodiment of FIG. 8, an optical amplitude modulator 111, such as a mechanical chopper, is provided in the path of the optical pump field, to introduce an amplitude modulation in the pump and Stokes signal 122.

Preferably, the pump and Stokes signals 119 and 120 are combined by an optical combination device 115, such as a dichroic mirror, to form the optical pump and Stokes beam 122. The (modulated) pump and Stokes beam 122 is combined (i.e. collinearly overlapped, because the beams are coherent) with the anti-Stokes signal 121 by means of a dichroic mirror 117 to form a combined optical signal 123 (i.e. the CARS analysis signal) which is directed to a per se known CARS microscope or spectroscope 118.

The analysis signal 123 impinges upon a specimen being analyzed (not shown in the figure) arranged within the CARS apparatus 118 and is Raman scattered from the specimen, thereby forming an optical Raman-scattering signal which is detected by a detector 124, such as a photomultiplier. In the specimen being analyzed the CARS optical field is directly mixed with the optical field of the local oscillator to be measured by the detector 124. The detected (electric) signal is transmitted to a lock-in amplifier 125 which extracts the signal component synchronous with the phase modulation, i.e. the heterodyne component. The electric signal at the output of the lock-in amplifier 125 can be transmitted to a computer for analysis and processing of the CARS spectra scattered from the specimen. Preferably, the amplitude modulator 111 is electrically controlled by the lock-in amplifier 125 by means of a feedback loop (not shown in the figure) allowing demodulation in the detected electric signal to be synchronous to the modulation introduced by the optical modulator.

The intensity I of the electric signal resulting from the interaction of the electric fields $E_{OL}$ and $E_{CARS}$ is given by $$I = E_{CARS}^2 + E_{OL}^2 + 2 E_{CARS} E_{OL} \cos(\Delta\Phi), \quad (1)$$

where the last term is the heterodyne (or interferometric) component that depends on the phase difference $\Delta\Phi$ between the two fields. Since the CARS and OL (local oscillator) electric fields are generated from a common pulse train, they are coherent and hence $\Delta\Phi$ remains constant with time and may be particularly set as 0. As the lock-in amplifier detects only the signal component proportional to the CARS signal (i.e. the $E_{OL}^2$ component is 0), the intensity of the electric signal at the output of the lock-in amplifier, according to the relation (1), becomes $$I = E_{CARS}^2 + 2 E_{CARS} E_{OL}. \quad (2)$$

The intensity value of the relation (2) shall be compared with the intensity $I = E_{CARS}^2$, obtained without a local oscillator. Therefore, the CARS signal will be amplified by a $E_{OL}/E_{CARS}$ factor. It shall be noted that typically $E_{OL} >> E_{CARS}$ because $E_{OL}$ is directly generated by a SH process, whereas $E_{CARS}$ is the result of the interaction with a molecular species that may be present at low concentrations in the specimen to be analyzed.

Optionally, the SH signal generated by each of the three nonlinear optical crystals 106-108 passes through a focusing/collimating lens 109 and a SWP filter 110 that cuts off the background signal at fundamental frequencies.

In the scheme of FIG. 8, the amplitude modulator 111 is placed downstream from the SWP filter 110 along the optical path of the pump signal 119. Alternatively, the amplitude modulator might be disposed in the optical path of the Stokes signal 120.

Optionally, a mirror 113 is disposed in the optical path of the pump signal 119, to deflect the signal to an optical delay device 112 for any adjustment of the length of the signal optical path. Optionally, the Stokes signal 120 passes through an optical delay line 114 for adjustment of the optical path length. Optionally, the anti-Stokes signal 121 passes through an optical delay device 116, always for adjustment of its optical path length.

According to a preferred embodiment, at least one of the three crystals of the SH generating system is frequency-tunable.

Figure 9:
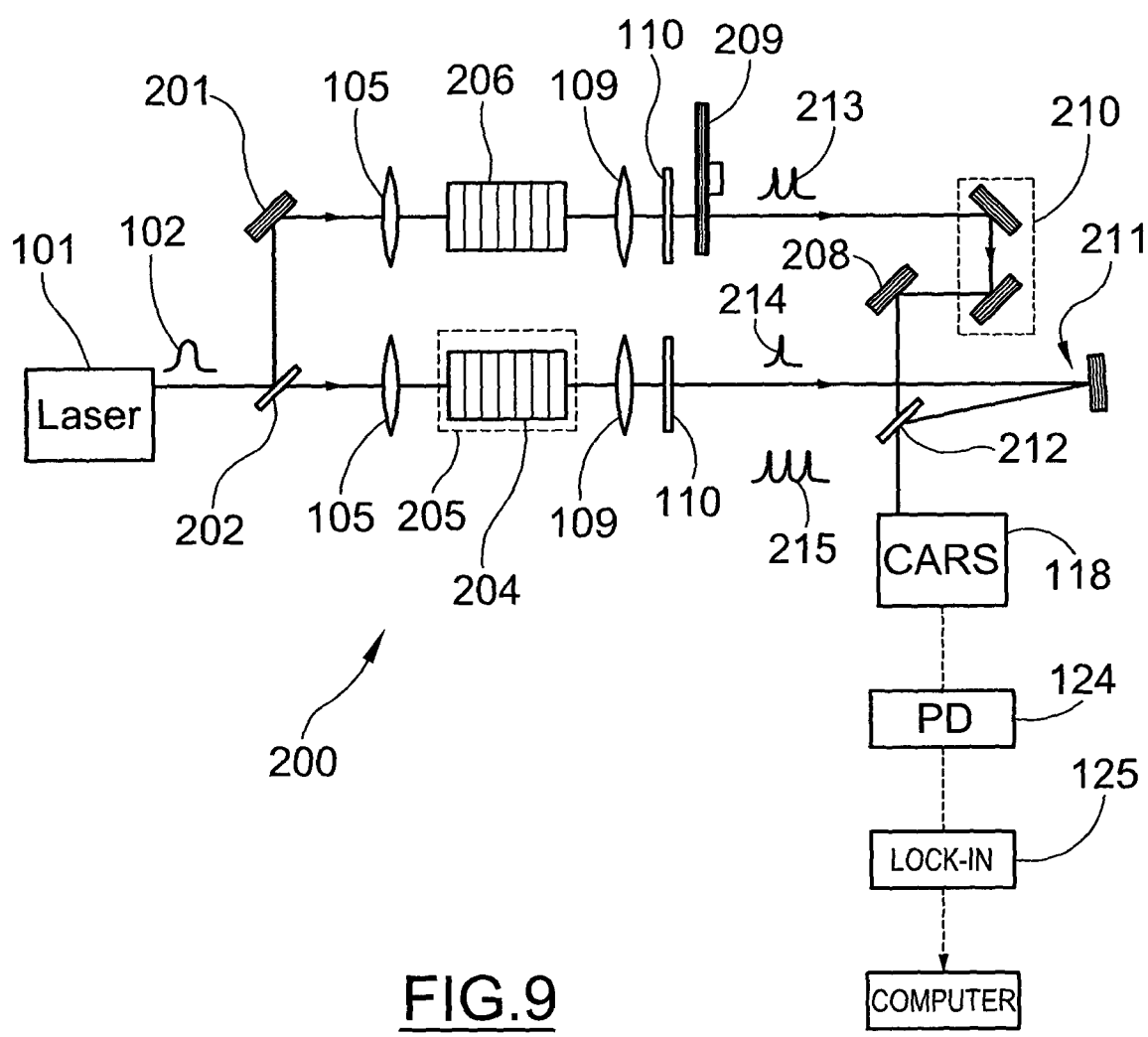
FIG. 9 is a diagrammatic view of a system for generating pulses for CARS that uses an optical heterodyne according to a further embodiment of the present invention.

FIG. 9 schematically shows a system for generating pulses 200 for heterodyne CARS according to a further embodiment of the present invention. Like reference numerals will be used to designate system components that are common with those of the system described with reference to FIG. 8 or have equivalent functions, detailed description thereof being omitted hereinafter. The main difference from the embodiment of FIG. 8 is that a single nonlinear optical crystal 206 is used in the part of the SH generating system apt to generate a pump signal $\omega_p$ and a Stokes signal of frequency $\omega_s$, which crystal is, in the preferred embodiments, an aperiodically poled (app) ferroelectric crystal of the type described with reference to FIG. 2. The signal of the local oscillator at anti-Stokes frequency $\omega_{as}$ is generated by a second nonlinear optical crystal 204, which is in the preferred embodiments a periodically poled (pp) ferroelectric crystal. Particularly, the fundamental pulse beam 102 emitted by the laser 101 is power-split by a power divider 202 which transmits a first part of the beam into the pp crystal 204 and deflects a second part of the beam towards a mirror 201 that directs it into the app crystal 206. The app crystal 206 generates a SH pulse beam 213 composed of two pulses at pump and Stokes frequencies (i.e. the CARS signal) and the crystal 205 generates a pulse beam 124 at the anti-Stokes frequency (i.e. the OL signal). An amplitude modulator 209 intercepts the SH signal that forms the CARS signal 213 and modulates its amplitude.

Optionally, the optical paths of the CARS signal 214 and the signal of the local oscillator 214 are adjusted by means of optical delay lines 210 and 211 respectively.

Preferably, the CARS signal is frequency-tunable by means of an app crystal 206 having a poling period variable in a direction transverse to the direction of propagation of the incident beam. Optionally, one of the two crystals (the crystal 204 in FIG. 9) is thermally controllable by means of an oven 205 that will receive the crystal for fine adjustment of the SH wavelength.

An optical recombination device, e.g., a dichroic mirror 212, combines the signal 213 (optionally deflected by a mirror 208) with the anti-Stokes OL signal 214 into an optical CARS analysis signal 215 which is supplied to a CARS apparatus 118.

Preferably, the amplitude modulator 209 is controlled by the lock-in amplifier 125, for example by means of a feedback loop, so as to allow demodulation in the detected electric signal to be synchronous to the modulation introduced by the optical modulator.

While the preferred embodiments of the present invention use crystals comprising pp or app ferroelectric materials, the SH generating systems of the present invention encompasses the use of nonlinear birefringent crystals without non periodically poling. Particularly, crystals may be used that have a nonzero second-order nonlinear optical susceptibility tensor, $\chi^{(2)}$, and are characterized by an ordinary index $n_o(\lambda)$, which depends on the wavelength of the incident beam $\lambda$, and an extraordinary refractive index $n_e(\theta,\lambda)$ that depends, besides of on the wavelength, on the angle $\theta$ of incidence formed by the beam with the main crystal axis of the material. The phase-matching condition in the birefringent material that produces SH generation is obtained by changing the angle of incidence of the beam with respect to the crystal. Birefringent crystals may be cut, using known techniques, in such a way that the normal angle of incidence is close to the angle corresponding to the phase-matching condition for a given fundamental wavelength.

Examples of birefringent crystals are $\beta$-BaBO$_4$, it LiB$_3$O$_5$ (LBO) and KTP. For these crystals, the SH frequency may be tuned by changing the angle formed by the normal at the entry face with the direction of incidence and hence by changing the direction of propagation within the crystal.

While the use of a single fs source is preferred to avoid the use of synchronization and/or phase-lock devices, the present invention may encompass the case of a CARS signal generating system having two distinct fs sources, which are synchronized, for instance, by two optical parametric amplifiers pumped by a femtosecond laser.

Advantageously, the system of the present invention allows synthesis of multi-colored, synchronous, phase-coherent and relatively narrow-band pulses (i.e. having a picoseconds duration in the time domain) by second-harmonic generation from a single femtosecond pulse train. The synthesized pulses may be used as pump and Stokes pulses in a CARS microscopy or spectroscopy system. In certain preferred embodiments, the generation of at least two second-harmonic pulses is obtained by two ferroelectric crystals with periodic space-modulation of the nonlinear susceptibility. In other preferred embodiments, the generation of at least two second-harmonic pulses is obtained by a single ferroelectric crystal with aperiodic spatial reversal of the sign of nonlinear optical susceptibility.

Advantageously, the system according to certain embodiments of the present invention allows to produce, by means of an additional nonlinear crystal with spatial variation of the nonlinear susceptibility, a third second-harmonic pulse synchronous and phase-coherent with the other two second-harmonic pulses, which can act as a local oscillator for heterodyne detection of the CARS signal. Therefore, it is possible to obtain a CARS signal amplified even by several orders of magnitude, with consequent increase of detection sensitivity and/or the speed of imaging acquisition.

According to certain embodiments of the present invention the system for generating CARS signals comprises a laser source apt to simultaneously generate two synchronous and phase-coherent pulses, yet having two different fundamental frequency bands, which are directed to a SH generating system comprising at least two nonlinear optical crystals and apt to generate three second-harmonic pulses at different frequencies, that may be alternately selected to obtain a CARS signal at two different vibrational frequencies.

The system of the present invention provides a source of multi-colored pulses for a CARS system, which can be frequency-tuned within a very broad frequency range, e.g. from $10\ cm^{-1}$ to $3500\ cm^{-1}$.

The invention claimed is:

1. A system for generating optical signals for Raman vibrational analysis of an external specimen, the system comprising:
    a laser source capable of emitting at least one femtosecond fundamental optical pulse in a first band of fundamental frequencies comprising at least one first ($\omega_{f1}$) and one second ($\omega_{f2}$) fundamental frequencies;
    a second-harmonic generating system comprising at least one nonlinear optical crystal capable of converting said at least one fundamental optical pulse into at least two second-harmonic optical pulses having a narrower band with respect to the bandwidth of the at least one fundamental pulse, a first second-harmonic pulse at a first second-harmonic frequency ($\omega_p$) of the first fundamental frequency ($\omega_{f1}$) and a second second-harmonic pulse at a second second-harmonic frequency ($\omega_s$) of the second fundamental frequency ($\omega_{f2}$), said second second-harmonic frequency being different from the first second-harmonic frequency, and
    a Raman vibrational analysis apparatus capable of receiving said first and second second-harmonic pulses and of directing them toward said specimen.

2. The system of claim 1, wherein said vibrational analysis apparatus is a CARS microscope or spectroscope that uses said first second-harmonic optical pulse as a pump signal and said second second-harmonic pulse as a Stokes signal.

3. The system of claim 1, wherein said at least one fundamental optical pulse has a time width of femtosecond order and each of said at least two second-harmonic pulses has time width of picosecond order.

4. The system of claim 1, further comprising:
    an optical power divider device capable of receiving said at least one fundamental optical pulse emitted from said laser source and of power dividing it into a first and a second fundamental pulse, said first and second fundamental optical pulses propagating along first and second optical paths respectively and impinging upon said second-harmonic generating system, wherein said second-harmonic generating system comprises a first nonlinear optical crystal arranged in the first optical path and capable of generating said first second-harmonic pulse and a second non-linear optical crystal arranged in the second optical path and capable of generating said second second-harmonic pulse, and an optical recombination device capable of receiving said first and second second-harmonic pulses from said first and second optical paths and of combining them into an optical Raman vibration analysis signal to be directed towards said specimen.

5. The system of claim 4, wherein each of said first and second nonlinear optical crystals includes a ferroelectric crystal having a periodic space modulation of the sign of the nonlinear optical susceptibility along their respective first and second optical paths.

6. The system of claim 4, wherein at least one of said first and second nonlinear optical crystals comprises a space modulation of the sign of the nonlinear optical susceptibility with a period varying along a direction transverse to its respective first and or second optical path.

7. The system of claim 4, wherein the laser source is capable of emitting an additional femtosecond fundamental optical pulse in a second band of fundamental frequencies comprising a third fundamental frequency ($\omega_{f3}$) different from the first ($\omega_{f1}$) and second ($\omega_{f2}$) fundamental frequencies, and
    the second-harmonic generating system comprises a third nonlinear optical crystal arranged in a third optical path, the third crystal being capable of receiving said additional fundamental optical pulse and of generating a third second-harmonic pulse at a third second-harmonic frequency of the third fundamental frequency ($\omega_{f3}$), and the optical recombination device is capable of receiving said third second-harmonic pulse from said third optical path and of selectively combining the first second-harmonic optical pulse with the second and third second-harmonic pulses to form the optical Raman vibrational analysis signal.

8. The system of claim 4, wherein said at least one fundamental pulse is in a second band of fundamental frequencies comprising a third fundamental frequency ($\omega_{f3}$) different from the first ($\omega_{f1}$) and second ($\omega_{f2}$) fundamental frequencies and
    the second-harmonic generating system comprises a third nonlinear optical crystal arranged in a third optical path, capable of receiving said at least one fundamental optical pulse and of generating a third second-harmonic pulse at a third second-harmonic frequency ($\omega_{as}$) of the third fundamental frequency, said third second-harmonic frequency being the anti-Stokes frequency with respect to the first and second second-harmonic frequencies, and the optical recombination device is capable of combining said first, second and third second-harmonic pulses into the optical Raman vibrational analysis signal.

9. The system of claim 1 further comprising:
    an optical power divider device capable of receiving said at least one fundamental optical pulse emitted from said laser source and of power dividing it into a first and a second fundamental pulse, said first and second fundamental optical pulses propagating along first and second optical paths respectively and impinging upon said second-harmonic generating system, wherein said second-harmonic generating system comprises a first nonlinear optical crystal arranged in the first optical path and capable of generating said first second-harmonic pulse and a second non-linear optical crystal arranged in the second optical path and capable of generating said second second-harmonic pulse, and an optical recombination device capable of receiving said first and second second-harmonic pulses from said first and second optical paths and of combining them into an optical Raman vibration analysis signal to be directed towards said specimen, and said at least one femtosecond fundamental pulse is in a second band of fundamental frequencies comprising a third fundamental frequency ($\omega_{f3}$) different from the first ($\omega_{f1}$) and second ($\omega_{f2}$) fundamental frequencies, the second-harmonic generating system comprises a third nonlinear optical crystal arranged in a third optical path, capable of receiving said at least one fundamental optical pulse and of generating a third second-harmonic pulse at a third second-harmonic frequency ($\omega_{as}$) of the third fundamental frequency, said third second-harmonic frequency being the anti-Stokes frequency with respect to the first and second second-harmonic frequencies, and the optical recombination device is capable of combining said first, second and third second-harmonic pulses into the optical Raman vibrational analysis signal, the system further comprising: an amplitude modulator arranged in said first or second optical paths downstream from the respective nonlinear optical crystal, said amplitude modulator being capable of modulating said first or second second-harmonic pulse, and an optical detector capable of receiving a Raman scattering signal that has been scattered from the external specimen by the Raman vibrational analysis beam and of converting it into an electric signal, and a lock-in amplifier capable of receiving the electric signal and of extracting the modulated component of said electric signal.

10. The system of claim 1, wherein said at least one fundamental pulse propagates along a first optical path in which said at least one nonlinear optical crystal is arranged, said at least one crystal comprising a ferroelectric crystal having an aperiodic space-modulation of the sign of the nonlinear optical susceptibility with a period varying along the first optical path, said crystal being capable of generating said first and second second-harmonic pulses.

11. The system of claim 10, wherein at least said ferroelectric crystal has a space-modulation of nonlinear optical susceptibility with a period varying along a direction transverse to the first optical path.

12. The system of claim 10, further comprising an optical recombination device capable of receiving said first and second second-harmonic pulses and wherein the laser source is capable of emitting an additional fundamental optical pulse in a second band of fundamental frequencies comprising at least one third fundamental frequency ($\omega_{f3}$) different from the first and second fundamental frequencies, and the second-harmonic generating system further comprises a second nonlinear optical crystal arranged in a second optical path, the second crystal being capable of receiving the additional femtosecond fundamental optical pulse propagating along the second optical path and to generate a third second-harmonic pulse at a third second-harmonic frequency of the third fundamental frequency, and the optical recombination device is capable of receiving said third second-harmonic pulse from said second optical path and of selectively combining the first second-harmonic optical pulse with the second and third second-harmonic pulses to form an optical Raman vibrational analysis signal.

13. The system of claim 1, wherein said at least one fundamental pulse propagates along a first optical path in which said at least one nonlinear optical crystal is arranged, said at least one crystal comprising a ferroelectric crystal having an aperiodic space-modulation of the sign of the nonlinear optical susceptibility with a period varying along the first optical path, said crystal being capable of generating said first and second second-harmonic pulses, the system further comprising an optical recombination device capable of receiving said first and second second-harmonic pulses and wherein said at least one fundamental pulse is in a second band of fundamental frequencies comprising a third fundamental frequency ($\omega_{f3}$) different from the first ($\omega_{f1}$) and second ($\omega_{f2}$) fundamental frequencies, and the second-harmonic generating system further comprising a second nonlinear optical crystal arranged in a second optical path, the second crystal being capable of receiving said at least one fundamental optical pulse and of generating a third second-harmonic pulse at a third second-harmonic frequency ($\omega_{as}$) of the third fundamental frequency, said third second-harmonic frequency being the anti-Stokes frequency with respect to the first and second second-harmonic frequencies, and the optical recombination device is capable of combining said first, second and third second-harmonic pulses into an optical Raman vibrational analysis signal.

14. The system of claim 1, wherein said at least one fundamental pulse propagates along a first optical path in which said at least one nonlinear optical crystal is arranged, said at least one crystal comprising a ferroelectric crystal having an aperiodic space-modulation of the sign of the nonlinear optical susceptibility with a period varying along the first optical path, said crystal being capable of generating said first and second second-harmonic pulses, the system further comprising an amplitude modulator arranged in said first optical path downstream from the aperiodically space-modulated ferroelectric crystal, said amplitude modulator being capable of modulating said first and second second-harmonic pulses, and an optical detector for receiving a Raman scattering signal that has been scattered from the external specimen by the Raman vibrational analysis beam and to convert it into an electric signal, and a lock-in amplifier for receiving the electric signal and extract the modulated component of said electric signal.

* * * * *